United States Patent
Dai et al.

(10) Patent No.: US 6,822,127 B2
(45) Date of Patent: Nov. 23, 2004

(54) SELECTIVE HYDROGENATION CATALYST FOR SELECTIVELY HYDROGENATING OF UNSATURATED OLEFIN, PROCESS FOR PREPARING THE SAME AND ITS USE

(75) Inventors: Wei Dai, Beijing (CN); Jing Zhu, Beijing (CN); Hui Peng, Beijing (CN); Yanlai Guo, Beijing (CN); Wei Mu, Beijing (CN); Helong Li, Beijing (CN); Qingzhou Cui, Beijing (CN)

(73) Assignees: China Petroleum & Chemical Corporation, Beijing (CN); Beijing Research Institute of Chemical Industry, China Petroleum & Chemical Corporation, Beijing (CN)

( * ) Notice: Subject to any disclaimer, the term of this patent is extended or adjusted under 35 U.S.C. 154(b) by 383 days.

(21) Appl. No.: 09/965,868

(22) Filed: Oct. 1, 2001

(65) Prior Publication Data

US 2002/0068843 A1 Jun. 6, 2002

(30) Foreign Application Priority Data

Sep. 29, 2000 (CN) ..................................... 00 1 24994 A

(51) Int. Cl.[7] ............................. C07C 5/02; B01J 23/63; B01J 23/50; B01J 23/644; B01J 23/68
(52) U.S. Cl. ....................... 585/259; 585/260; 585/262; 502/328; 502/329; 502/330; 502/331; 502/353
(58) Field of Search ................................. 585/259, 260, 585/262; 502/328, 329, 330, 331, 353

(56) References Cited

U.S. PATENT DOCUMENTS

| | | | | |
|---|---|---|---|---|
| 2,511,453 | A | * | 6/1950 | Barry .......................... 585/262 |
| 3,325,556 | A | | 6/1967 | De Rosset |
| 3,489,809 | A | | 1/1970 | Keith et al. |
| 3,900,526 | A | | 8/1975 | Johnson et al. |
| 3,912,789 | A | | 10/1975 | Frevel et al. |
| 4,404,124 | A | | 9/1983 | Johnson et al. |
| 4,490,481 | A | | 12/1984 | Boitiaux et al. |
| 4,577,047 | A | | 3/1986 | Hudson |
| 5,426,253 | A | | 6/1995 | Morikawa et al. |
| 6,228,800 | B1 | * | 5/2001 | Yamaguchi et al. ........ 502/339 |

FOREIGN PATENT DOCUMENTS

| | | | |
|---|---|---|---|
| CN | 1151908 A | 6/1997 | |
| CN | 1279126 A | 1/2001 | |
| DE | 1 284 403 | 12/1968 | |
| EP | 0 089 252 | 9/1983 | |
| WO | WO 9826867 A1 | * 6/1998 | ............ B01J/23/44 |

* cited by examiner

*Primary Examiner*—Walter D. Griffin
(74) *Attorney, Agent, or Firm*—Finnegan, Henderson, Farabow, Garrett & Dunner, L.L.P.

(57) ABSTRACT

A selective hydrogenation catalyst for the seletive hydrogenation of unsaturated hydrocarbons, a process for preparing this catalyst and its use. The catalyst of the invention comprises a support, active component Pd, rare earth metals, and auxiliary metal Bi, Ag etc. The catalyst is able to hydrogenate high-unsaturated hydrocarbons such as alkyne with high selectivity at high space velocity while both green oil formation and carbon deposition on the catalyst are very low. It is applicable to an industrial cracking process.

19 Claims, No Drawings

SELECTIVE HYDROGENATION CATALYST FOR SELECTIVELY HYDROGENATING OF UNSATURATED OLEFIN, PROCESS FOR PREPARING THE SAME AND ITS USE

FIELD OF THE INVENTION

This invention relates to a selective hydrogenation catalyst for the selective hydrogenation of unsaturated hydrocarbons, a process for preparing this catalyst and its use, more specifically, to the selective hydrogenation catalyst for selectively hydrogenating acetylenic and diolefinic compounds having two to four carbon atoms into corresponding olefin and its use in petroleum hydrocarbon thermal cracking process.

BACKGROUND OF THE INVENTION

It is well known that the steam cracking of petroleum hydrocarbon is the most important process for manufacturing the monomers of polyolefin such as ethylene, propylene. Its process route is that after mixing petroleum hydrocarbon with steam, the mixture stream in cracking furnace is thermal cracked at 750–870° C. to form $H_2$, CO, $CO_2$ and the mixture of saturated and unsaturated aliphatic hydrocarbons having one to three carbon atoms and aromatic hydrocarbons. By passing through a series of fractionating towers, the feed stream is fractionated into fractions of $>C_{10}$, $H_2$ and $CH_4$, $C_2$, $C_3$, $C_4$, $C_5$–$C_{10}$. In $C_2$–$C_{10}$ fractions, there exist unsaturated hydrocarbons such as mono-olefin, alkyne, diolefin etc. The alkyne and diolefin in $C_2$, $C_3$ fractions are the poisonous impurities which interfere the follow up polymerizations of ethylene, and propylene. They make the activity of polymerization catalyst decrease and catalyst consumption increase, moreover the performance of polymerization product poor. It is needed to control strictly the amount of diolefin and alkyne such as acetylene contained in the cracked product. In recent years, the high efficiency catalyst for the polymerization of ethylene newly developed gets more and more strict on the concentration requirement of alkyne and polyolefin. For example, for $C_2$ fraction, the acetylene content was limited to $10^{-6}$ mol % or less after 1980's, and for some process having special requirement such as the manufacture of HDPE, the acetylene content in refined ethylene was limited to $0.1 \times 10^{-6}$ mol % or less.

Therefore, how to remove more efficiently the highly unsaturated hydrocarbon such as acetylene from the cracked product has been concerned generally. In general, the catalytically selective hydrogenation method is adopted to remove the acetylene in ethylene-ethane fraction. In the reaction of selective hydrogenation for acetylene removal, the whole acetylene should be converted while no over-hydrogenation occurs such that ethylene loss is avoided. Consequently, both the superior activity and higher selectivity of the hydrogenation catalyst are required. Moreover, the acetylene absorbed on catalyst surface is easily dimerized through hydrogenation to form unsaturated $C_4$ hydrocarbons such as 1,3-butadiene, and such a $C_4$ hydrocarbon would react subsequently with acetylene or ethylene or other unsaturated hydrocarbon to form $C_6$–$C_{24}$ oligomers (known as 'green oil'). A part of so-called green oil, flowing along with the feed stream, is removed in a green oil absorber, and the other part would adhere on the catalyst surface and cover on the active center of catalyst, which will make its hydrogenation activity and selectivity decrease gradually, shorten the catalyst operation cycle period and lead to more frequent regeneration, affect the service life, thus increase in production costs. Therefore, the selective hydrogenation catalyst having superior performance should have high activity, selectivity and lower amount of green oil formation, particularly the amount of green oil adhered on the catalyst should be low.

In the prior art, generally a large quantity of supported Pd catalyst is adopted and other cocatalyst component added. For example, cocatalyst component disclosed in U.S. Pat. No. 4,404,124 is Ag, that in EP892,252 is Au, that in DE 1,284,403 and U.S. Pat. No. 4,577,047 is Cr, that in U.S. Pat. No. 3,912,789 is Cu, that in U.S. Pat. No. 3,900,526 is Fe, that in U.S. Pat. No. 3,489,809 is Rh, that in U.S. Pat. No. 3,325,556 is Li, that in CN1151908A is K; moreover other cocatalyst components disclosed include Pb, Zn etc.

In above-mentioned cocatalyst components disclosed, some of them sacrificed Pd catalyst's selectivity due to improving its activity, some of them can improve the Pd catalyst's selectivity or reduce the green oil formation, but their activity reduced significantly. Consequently, only the Pd—Ag catalyst is in common use industrially at present. But with respect to its activity and selectivity, Pd—Ag catalyst is still less than satisfactory, particularly the control of green oil formation on catalyst surface is undesirable yet.

In connection with the above disadvantages, a selective hydrogenation catalyst for alkyne is disclosed in the Chinese Patent Application CN 1,279,126A, wherein the main catalyst component is Pd and cocatalyst component is Bi and Ag. When the catalyst system is used in the selective hydrogenation of alkyne, it reduces green oil formation obviously while exhibits higher activity and selectivity, thus the carbon deposit decrease and service life of the catalyst increase.

However, said catalyst is still less than satisfactory. Along with the increasing of alkyne handling capacity in industrial application and the aggravation of side reaction at severer reaction conditions such as high space velocity (7,000–20,000 $hr^{-1}$) and high alkyne content, the activity, selectivity, the regeneration period and service life of said catalyst are unsatisfactory, improvements thereof are still needed. In general, the catalytic ability of the catalyst decreases due to deposition of carbon on the catalyst after a long time of alkyne selective hydrogenation, and the catalyst should be regenerated by heating to about 500° C. with air blow so as to recover the activity and selectivity if it fail to meet the production requirement even at an elevated temperature. The temperature, at which a catalyst is regenerated, must be controlled strictly. But even so, the technical parameters of the catalyst such as specific surface area and the like are also changed greatly after enduring 3–5 times of regeneration. The poor repeatability and stability of catalyst will result in the deterioration of its properties until it can not be used again and must be substituted with a new catalyst.

It is known that rare earth metals can be used in hydrogenation catalyst wherein Pd acts as main active component. For example, in U.S. Pat. No. 5,426,253, a process for hydrogenating 2,2-dichloro-1,1,1,2-tetrafluoroethane and 2-chloro-1,1,1,2-tetrafluoroethane or a mixture thereof into 1,1,1,2-tetrafluoroethane is disclosed, wherein the main active component of the adopted catalyst is a metal of Group VIII selected from the group consisting of Pt, Pd, Ni, Rh, Co. Ru and Ir. Moreover, said catalyst contains at least one of the following metals: Cu, Ag, Au, La, Ce and Nd, and which is disclosed to be used as the cocatalyst with a corrosion-resistance in the hydrogenation and dechlorination of halohydrocarbon concerned in this patent so as to protect the activity of the catalyst from the influence of HCl formed in the dechlorination.

As a result of making repeated experiments, the present inventors discover that by means of the supporter loaded concurrently main active component Pd, cocatalyst component Bi, rare earth metals and at least one of Ag, Cu, K, Na, Sr, Mn, Zr, Mo, Co, Ge, or a combination of two or more metals thereof, the hydrogenation reaction of acetylene is carried out in higher selectivity and higher activity under a high space velocity, wherein said acetylene exists in the $C_2$ fraction resulted from petroleum hydrocarbon thermal cracking process. Moreover, the catalyst of the present invention has the advantage of good stability, small changes in catalyst's properties after multiple times regenerations, easily controllable physical parameters, improved regeneration period and service life due to the addition of rare earth metals.

SUMMARY OF THE INVENTION

The object of this invention is to provide a selective hydrogenation catalyst for selectively hydrogenating unsaturated olefin.

Another object of this invention is to provide a process for preparing this catalyst.

A further object of this invention is to provide a use of said catalyst in the petroleum hydrocarbon thermal cracking process for selectively hydrogenating $C_2$ fraction or $C_3$ fraction including high-unsaturated hydrocarbons such as acetylene etc. into olefin.

A selective hydrogenation catalyst for selectively hydrogenating unsaturated hydrocarbon of the present invention, which comprises mainly the following active components loaded on a porous inorganic supporter:

(1) at least one of Pt, Pd, Ni, Ru, Co, and Rh;
(2) at least one of Ag, Cu, Zn, K, Na, Mg, Ca, Be, Sn, Pb, Sr, Ba, Ra, Fe, Mn, Zr, Mo, and Ge;
(3) at least one of rare earth metals; and
(4) Bi;

wherein the rare earth metal is selected from Sc, Y, and Lanthanides in Group IIIB of periodic table of elements.

The preparation method of the catalyst of the present invention is: the rare earth metal component being loaded first, or the rare earth metal component and K or Na component being loaded concurrently first, and then other active components being loaded stepwise or concurrently.

DETAILED DESCRIPTION OF THE INVENTION

This invention is described hereinafter in detail.

It is understood that this invention is not limited to the specific compositions, steps and materials and modifications on these compositions, steps and materials can be made under the spirit of the present invention. It should be pointed out that the terms used herein are only descriptive but they cannot be conceived as limit to the scope of the invention.

The selective hydrogenation catalyst of this invention for selectively hydrogenating unsaturated olefin comprises mainly the following active components loaded on a porous inorganic supporter:

(1) at least one of Pt, Pd, Ni, Rh, Co, and Ru;
(2) at least one of Ag, Cu, Zn, K, Na, Mg, Ca, Be, Sn, Pb, Sr, Ba, Ra, Fe, Mn, Zr, Mo, and Ge;
(3) at least one of rare earth metals; and
(4) Bi;

wherein the rare earth metal is selected from Sc, Y and Lanthanides including La, Ce, Pr, Nd, Pm, Sm, Eu, Gd, Tb, Dy, Ho, Er, Tm, Yb, and Lu.

Based on the total weight of the metal elements, the amount of active component(1), for each 100% by weight of the catalyst (hereinafter the percentage being based on the weight ratio of metal elements) is 0.001–1%, preferably 0.008–0.3%, more preferably 0.01–0.15%. The preferred component (1) is Pd or Pt.

Based on the total weight of the metal elements, the amount of active component(2), for each 100% by weight of the catalyst, is 0.001–10%, preferably 0.01–2%. The preferred active component (2) is at least one of Ag, K, Na, Zn, Sn, Pb, and Cd, more preferably Ag or Ag and K or Ag and Na.

It should be particularly noted that according to the performance requirement for the final catalyst, two or more metals, such as Ag and alkali metal Na or K, can be used together, and made to improve the catalyst performances obviously.

The weight percentage (wt. %) of active component (3), for each 100% by weight of the catalyst, is 0.01–5%, preferably 0.05–3%, more preferably 0.1–1.5%. The preferred rare earth metal is La, Ce, Nd, Pm, Eu, Y or mixtures thereof, more preferably La and/or Nd. The rare earth metal content loaded on the supporter has direct influence on the performance of the final catalyst of the invention. Generally, when the content of the rare earth metal is less than 0.01%, its stabilizing effect and promoter action on the catalyst would not be very obvious, the invention fails to be achieved; however, when the content is higher than 5%, such a high amount not only makes the catalyst cost up, but also influence fairly on the performances, such as activity and selectivity of the catalyst.

The weight percentage of active component (4), for each 100% by weight of catalyst, is 0.001–5%, preferably 0.005–1%.

The porous inorganic supporter of the invention can be the well-known supporter in the prior art. For example, diatomaceous earth, spinel, $SiO_2$, $TiO_2$, $Al_2O_3$, or mixtures thereof. The preferred supporter of the invention is $Al_2O_3$ or $SiO_2$; Its shape can be granular, gear-shaped, spherical, lamninar or strip, preferably gear-shaped or spherical, more preferably gear-shaped (such a shape has an advantage of low bed pressure drop at high space velocity); its specific surface area is 1–200 $m^2/g$, preferably 2–120 $m^2/g$, more preferably 2–50 $m^2/g$.

It should be particularly noted that the gear-shaped supporter is preferably used in the catalyst of the invention for industrial application. As a result of the increase of space velocity in selective hydrogenation, the increase of the pressure drop of catalyst bed would have certain influence on the normal operation at downstream section. When the space velocity increases, the pressure drop of the catalyst made of gear-shaped supporter, and of spherical supporter both increase to some extent, but the speed gain of pressure drop of spherical supporter is higher than that of gear-shaped supporter. Therefore, in higher space velocity hydrogenation, the gear-shaped supporter chosen is superior to spherical supporter.

For the preparation of the catalyst of the invention, the well-known conventional method such as impregnating and spraying can be used to load said active components on the supporter stepwise or concurrently.

The preferred preparation method is: the rare earth metal component being loaded fist, or the rare earth metal component and K or Na component being loaded concurrently first, and then other active components loaded stepwise or concurrently.

The most preferred method is:
(1) Adding the salt solution of rare earth metal into the supporter forming materials during the formation of the supporter; or impregnating the supporter after the formation of the supporter with an aqueous solution of rare earth metal salt, drying and calcining, the preferred rare earth metal salt solution is its nitrate solution;
(2) Impregnating concurrently or separately said supporter with the salt solution of component(1), salt solution of component(2) and salt solution of component(4), after drying at 100–300° C. for 5–24 hr, calcining at 350–900° C. for 4–20 hr to obtain the catalyst.

When the active component (1) is Pd, the suitable examples of palladium salt include (but not limit to) palladium chloride, palladium bromide, palladium iodide, palladium acetate, palladium nitrate, palladium sulfate, palladium acetylacetonate, and mixtures of any two or more thereof. For convenience, the preferred palladium compound is palladium chloride and/or palladium nitrate.

When the active component (2) is Ag, the suitable examples of the silver salt include (but not limit to) silver nitrate, silver fluoride, silver perchlorate, and mixtures of any two or more thereof. For convenience, the preferred silver compound is an aqueous solution of silver nitrate.

When the active component (2) is potassium or sodium, the suitable examples of the alkali metal compound include (but not limit to) potassium (or sodium) nitrate, potassium (or sodium) halide, K(or Na) $XO_3$ (wherein X=halogen), potassium (or sodium) phosphate, potassium (or sodium) hydrogen phosphate, potassium (or sodium) carbonate, potassium (or sodium) hydrogen carbonate, potassium (or sodium) salts of organic acids, potassium (or sodium) hydrate, potassium (or sodium) molybdate, potassium (or sodium) sulfate, potassium (or sodium) arsenate and mixtures of any two or more thereof. For convenience, the preferred alkali metal compound is an aqueous solution of potassium (or sodium) hydrate.

When the active component (3) is rare earth metal, the suitable examples of the rare earth element compound include (but not limit to) its nitrate, halide, salt of organic acid, and mixtures of any two or more thereof. For convenience, the preferred rare earth element compound is an aqueous solution of nitrate solution.

When the active component (4) is Bi, the suitable examples of bismuth salt includes (but not limit to) bismuth nitrate, and bismuth chloride.

It should be noted that, it is advantageous to impregnate the supporter with the maximum amount of the salt solution of active component absorbable by the supporter.

It is observed clearly through scanning electron microscope (SEM) that the active component(1), such as Pd, in the catalyst of the invention disperses uniformly on catalyst surface and forms a very thin Pd layer with a thickness of 1 to 30 μm, in generally. In connection with the selective hydrogenation which is mainly a diffusion-controlled reaction, the catalyst to be used therein with a thinner thickness of Pd layer will be advantageous to make the activity and selectivity of the catalyst higher.

The catalyst of the invention is applicable to all the selective hydrogenation for high unsaturated hydrocarbon to corresponding olefin, especially applicable to the petroleum hydrocarbon thermal cracking selective hydrogenation for the $C_2$ fraction containing high unsaturated hydrocarbon such as acetylene to olefin. The term "high unsaturated hydrocarbon" herein is referred to the hydrocarbons containing triple bond and/or two or more double bonds. The term "petroleum hydrocarbon thermal cracking process selective hydrogenation" throughout the specification means both "front end hydrogenation" and "back end hydrogenation" well known by persons skilled in the art. The catalyst of the invention also is applicable to the removal of trace acetylene from refined ethylene so as to obtain the product which satisfies with the standard of polymerizing grade ethylene.

In service to said hydrogenation, the selective hydrogenation catalyst of the invention demonstrates the following outstanding results:

(1) The synergistic effect of the multiple active components in the catalyst of present invention makes the activity and selectivity of the catalyst increase, the green oil formation reduce, the carbon deposition of long duration decrease, thus the service period is lengthened over a wider ranger, the service life of the catalyst is increased.

(2) The Pd layer on the catalyst is very thin (1–30 μm). This kind of thin Pd layer is favorable to the diffusion of reactants, especially at higher space velocity (higher concentration of reactants and larger material handling capacity), the catalyst still has higher activity and selectivity. So it is very applicable to industrial cracking process.

(3) The stability of catalyst is improved obviously, thus both the activity and selectivity of the catalyst are made to increase.

(4) Moreover, the gear-shaped supporter adopted makes the catalyst be able to operate stably at high space velocity, increase greatly the handling capacity of the catalyst.

In brief, the catalyst of the invention is able to cay out hydrogenation of alkyne or diolefin high selectively and high actively at higher space velocity, moreover maintain low green oil formation, and the catalyst has the advantage of long regeneration period, long service life and low cost.

EXAMPLES AND COMPARATIVE EXAMPLES

Example 1

20 g of gear-shaped alumina were put into a beaker. Lanthanum nitrate solid was weighed out precisely to such an amount that made a finally obtained catalyst of this Example contain 0.5 wt. % of La. A lanthanum nitrate aqueous solution was prepared by dissolving and diluting the lanthanum nitrate solid with water into a maximal volume which the gear-shaped alumina could absorb. The gear-shaped alumina was impregnated with the lanthanum nitrate aqueous solution, after drying at 120° C. for 4 hours and calcining at 1100° C. for 4 hours, a La-loaded alumina was obtained. A suitable amount of palladium nitrate solution was weighed out so as to make the finally obtained catalyst contain 0.03 wt. % of Pd. The palladium nitrate solution was diluted with water to a maximal volume which the gear-shaped alumina could absorb. The La-loaded alumina was impregnated with the diluted palladium nitrate aqueous solution, after drying at 120° C., a Pd—La/alumina catalyst was obtained. A suitable amount of silver nitrate solid was weighed out precisely so as to make the finally obtained catalyst contain 0.07 wt. % of Ag. The silver nitrate solid was dissolved in water which volume was equal to that of above aqueous solution of palladium nitrate. The Pd—La/alumina catalyst was impregnated with the silver nitrate aqueous solution, after drying at 120° C., a Pd—La—Ag/alumina catalyst was obtained. A suitable amount of bismuth nitrate solid was weighed out precisely so as to make the finally obtained catalyst contain 0.03 wt. % of Bi. The bismuth nitrate solid was dissolved in the water which volume was equal to that of above aqueous solution of palladium nitrate. The Pd—La—Ag/alumina catalyst was impregnated with the bismuth nitrate aqueous solution, after drying at 120° C. and calcining at 450° C. for 4 hours, a 0.03 wt. % Pd–0.5 wt. % La–0.07 wt. % Ag–0.03 wt. % Bi/alumina catalyst was obtained.

Comparative Example 1

A 0.03 wt. % Pd–0.07 wt. % Ag–0.03 wt. % Bi/alumina catalyst was prepared according to the same method as described in Example 1, except the gear-shaped alumina was not impregnated with an aqueous solution of lanthanum nitrate.

Comparative Example 2

A 0.03 wt. % Pd–0.5 wt. % La–0.07 wt. % Ag/alumina was prepared according to the same method as described in Example 1, except the Pd—La—Ag/alumina catalyst was not impregnated with bismuth nitrate aqueous solution.

Example 2

The gear-shaped alumina was loaded successively with lanthanum nitrate, potassium hydrate, palladium nitrate, silver nitrate and bismuth nitrate by impregnating and drying to obtain a Pd—La—Ag—K—Bi/alumina catalyst. After calcining the Pd—La—Ag—K—Bi/alumina catalyst at 450° C. for 4 hours, a 0.03 wt. % Pd–0.1 wt. % K–0.5 wt. % La–0.07 wt. % Ag–0.03 wt. % Bi/alumina catalyst was obtained.

Example 3

A 0.033 wt. % Pd–0.1 wt. % K–0.03 wt. % La–0.33 wt. % Ag–0.005 wt. % Bi/alumina catalyst was prepared according to the same method as described in Example 2.

Comparative Example 3

A 0.03 wt. % Pd–0.1 wt. % K–0.07 wt. % Ag–0.03 wt. % Bi/alumina catalyst was prepared according to the same method as described in example 2, except the gear-shaped alumina was not impregnated with aqueous solution of lanthanum nitrate.

A micro-counter estimation unit was used to evaluate the catalysts of Examples 1–3 and Comparative Examples 1–3. The packing quantity of the catalyst was 1 ml and the packing height of it was 20 mm. The evaluation was conducted under the following conditions: $H_2$/alkyne=1.3, reaction temperature: 130° C., inlet concentration of alkyne: 0.51%, space velocity: 10,000 $hr^{-1}$. The results were shown in Table 1.

TABLE 1

| Example # | Supporter | Catalyst components | Pd (wt. %) | Rare earth metal (wt. %) | K (wt. %) | Ag (wt. %) | Bi (wt. %) | Thickness of Pd layer (μm)* | Acetylene conversion(%) | Ethylene Selectivity (%) |
|---|---|---|---|---|---|---|---|---|---|---|
| Comparative Example 1 | Gear-shaped alumina | Pd—Ag—Bi | 0.03; palladium nitrate | | | 0.07; silver nitrate | 0.03; bismuth nitrate | 5–70 | 90 | 80 |
| Comparative Example 2 | Gear-shaped alumina | Pd—La—Ag | 0.03; palladium nitrate | 0.5; lanthanum nitrate | | 0.07; silver nitrate | | | 95 | 75 |
| Comparative Example 3 | Gear-shaped alumina | Pd—Ag—Bi—K | 0.03; palladium nitrate | | 0.1; potassium hydrate | 0.07; silver nitrate | 0.03; bismuth nitrate | 5–40 | 95 | 87 |
| Example 1 | Gear-shaped alumina | Pd—La—Ag—Bi | 0.03; palladium nitrate | 0.5; lanthanum nitrate | | 0.07; silver nitrate | 0.03; bismuth nitrate | 5–30 | 100 | 85 |
| Example 2 | Gear-shaped alumina | Pd—La—K—Ag—Bi | 0.03; palladium nitrate | 0.5; lanthanum nitrate | 0.1; potassium hydrate | 0.07; silver nitrate | 0.03; bismuth nitrate | 1–20 | 100 | 92 |
| Example 3 | Gear-shaped alumina | Pd—La—K—Ag—Bi | 0.033; palladium nitrate | 0.03; lanthanum nitrate | 0.1; potassium hydrate | 0.33; silver nitrate | 0.005; bismuth nitrate | | 92 | 82 |

*The thickness of Pd layer is determined by reducing the catalyst firstly according to conventional methods in the art, and then measuring by SEM.

As the results shown in Table 1, both the acetylene conversion and the ethylene selectivity are improved obviously by using the Pd—La—Ag—Bi/alumina catalyst and Pd—La—Ag—K—Bi/alumina catalyst of the present invention.

Example 4

300 g of alumina spheres were weighed out precisely. A 0.03 wt. % Pd–0.5 wt. % La–0.186 wt. % Ag–0.12 wt. % Bi/alumina catalyst was prepared according to the same method as described in Example 1.

Example 5

A 0.03 wt. % Pd–1.0 wt. % La–0.186 wt. % Ag–0.12 wt. % Bi/alumina catalyst was prepared according to the same method as described in Example 4, except the amount of lanthanum nitrate was changed.

Comparative Example 4

A 0.03 wt. % Pd–0.186 wt. % Ag–0.12 wt. % Bi/alumina catalyst was prepared according to the same method as described in Example 4, except the alumina was not impregnated with an aqueous solution of lanthanum nitrate.

Comparative Example 5

A 0.03 wt. % Pd–0.18 wt. % Ag/alumina catalyst was prepared according to the same method as described in Example 4, except the alumina was not impregnated with an aqueous solution of lanthanum nitrate and the Pd—Ag/alumina catalyst was not impregnated with an aqueous solution of bismuth nitrate.

Example 6

An aqueous solution of lanthanum nitrate was put into alumina powder to prepare gear-shaped supporter by conventional method. The gear-shaped supporter was impregnating successively with aqueous solutions of palladium nitrate, silver nitrate and bismuth nitrate, after drying and calcining, a 0.03 wt. % Pd–0.5 wt. % La–0.186 wt. % Ag–0.12 wt. % Bi/alumina catalyst was obtained.

Example 7

A 0.031 wt. % Pd–2.5 wt. % La–0.186 wt. % Ag–0.03 wt. % Bi/alumina catalyst was prepared according to the same method as described in Example 6.

Example 8

A 0.03 wt. % Pd–0.1 wt. % K–0.5 wt. % La–0.105 wt. % Ag–0.06 wt. % Bi/alumina catalyst was prepared according to the same method as described in Example 6.

Example 9

A 0.03 wt. % Pd–0.1 wt. % K–0.5 wt. % La–0.07 wt. % Ag–0.03 wt. % Bi/alumina catalyst was prepared according to the same method as described in Example 6.

The catalysts of Comparative Example 4, Comparative Example 5, and Examples 4–9 were chosen to perform hydrogenation experiments respectively.

200 ml of catalyst was packed into a tubular reactor; glass beads were packed on the top of the catalyst bed and under the bottom thereof. After displacing with nitrogen gas, and reducing, a fraction from the top of de-ethanizer of the back end hydrogenation process in ethylene cracking procedure was hydrogen-mixed and then passed from top to bottom through the reactor, in which the fraction contained 0.8–1.1 mol % of acetylene, 15–20 mol % of ethane and the balance of ethylene. The hydrogenation reaction was conducted under the following conditions: $H_2$/alkyne=1.5, inlet temperature of reactor: 35° C., space velocity: 10,000 $hr^{-1}$. The results were shown in table 2.

TABLE 2

| Example # | Supporter | Catalyst components | Component (1) (wt. %) | Component (2) (wt. %) | Component (3) (wt. %) | Component (4) (wt. %) | Outlet acetylene ($10^{-6}$ mol) | Ethylene selectivity (%) |
|---|---|---|---|---|---|---|---|---|
| Comparative Example 4 | Alumina sphere | Pd—Ag—Bi | 0.03; palladium chloride | 0.186; silver nitrate | | 0.12: bismuth nitrate | <1 | 45 |
| Comparative Example 5 | Alumina sphere | Pd—Ag | 0.03; palladium chloride | 0.18; silver nitrate | | | 33 | 29 |
| Example 4 | Alumina sphere | Pd—La—Ag—Bi | 0.03; palladium chloride | 0.186; silver nitrate | 0.5; lanthanum nitrate | 0.12; bismuth nitrate | <1 | 52 |
| Example 5 | Alumina sphere | Pd—La—Ag—Bi | 0.03; palladium chloride | 0.186; silver nitrate | 1.0; lanthanum nitrate | 0.12; bismuth nitrate | <1 | 50 |
| Example 6 | Gear-shaped alumina | Pd—La—Ag—Bi | 0.03; palladium chloride | 0.186; silver nitrate | 0.5; lanthanum nitrate | 0.12; bismuth nitrate | <1 | 49 |
| Example 7 | Gear-shaped alumina | Pd—La—Ag—Bi | 0.031; palladium chloride | 0.186; silver nitrate | 2.5; lanthanum nitrate | 0.03; bismuth nitrate | <1 | 35 |
| Example 8 | Gear-shaped alumina | Pd—La—K—Ag—Bi | 0.03; palladium chloride | 0.105;silver nitrate 0.1;potassium hydrate | 0.5; lanthanum nitrate | 0.06; bismuth nitrate | <1 | 61 |

TABLE 2-continued

| Example # | Supporter | Catalyst components | Component (1) (wt. %) | Component (2) (wt. %) | Component (3) (wt. %) | Component (4) (wt. %) | Outlet acetylene ($10^{-6}$ mol) | Ethylene selectivity (%) |
|---|---|---|---|---|---|---|---|---|
| Example 9 | Gear-shaped alumina | Pd—La—K—Ag—Bi | 0.03; palladium chloride | 0.07;silver nitrate 0.1;potossium hydrate | 0.5; lanthanum nitrate | 0.03; bismuth nitrate | <1 | 60 |

As the results shown in the table 2, the selectivity of catalyst is increased by more than 10% under the condition of higher space velocity of 10,000 hr$^{-1}$ due to the existing of rare earth metal component, which is very valuable to the industrial application of the catalyst.

Under the aforesaid conditions, after the catalysts of Comparative Example 2, Comparative Example 4, Example 4 and Example 5 reacting respectively for 943 hours, the collected amount of green oil and the weight gain of the catalyst (i.e. the total weight of green oil and carbon deposit on each catalyst) were measured carefully as shown in the following table 3.

TABLE 3

| Example # | Comparative Example 2 | Comparative Example 4 | Example 4 | Example 5 |
|---|---|---|---|---|
| Weight gain of a catalyst after reacting for 943 hr(g) | 16.20 | 14.66 | 9.24 | 9.01 |
| Green oil weight after reacting for 943 hr(g) | 120.1 | 115.8 | 107.4 | 96.6 |
| Color of green oil | Light yellow | Light yellow | Colorless | Colorless |

The lighter color of green oil indicates the smaller molecular weight of green oil, so that it is easier to be removed during catalyst regeneration. The smaller weight gain of the catalyst indicates the longer operating period of a catalyst. From the results shown in table 3, it is very clear that the weight gain of catalyst is reduced by more than 30% and the amount of green oil after reaction is decreased obviously due to the existing of rare earth metal element and Bi.

Example 10

20 g of formed gear-shaped alumina supporter were impregnated with an aqueons solution of lanthanum nitrate, so as to made a La-loaded supporter containing 0.1 wt. % of La. According to aforesaid preparation method, the La-loaded supporter was impregnated successively with aqueous solutions of palladium chloride, silver nitrate, bismuth nitrate, after drying and calcining, a 0.03 wt. % Pd–0.1 wt. % La–0.18 wt. % Ag–0.10 wt. % Bi/Alumina catalyst was obtained.

Example 11–15

Five catalysts were prepared according to the same method as described in Example 10, except aqueous solutions of cerium nitrate, neodymium nitrate, praseodymium nitrate, europium nitrate, yttrium nitrate were substituted for the aqueous solution of lanthanum nitrate respectively in each Example.

A micro-counter estimation unit was used to evaluate the catalysts of Examples 10–15. The packing quantity of the catalyst was 1 ml and the packing height of it was 20 mm. The evaluation was conducted under the following conditions: H$_2$/alkyne=1.5, reaction temperature: 90° C., inlet concentration of alkyne: 0.4 mol %, space velocity: 10,000 hr$^{-1}$. The results were shown in Table 4.

TABLE 4

| Example # | Supporter | Catalyst component | Pd (wt. %) | Ag (wt. %) | rare earth metal cocatalyst (wt. %) | Bi (wt. %) | Acetylene conversion(%) | Ethylene selectivity(%) |
|---|---|---|---|---|---|---|---|---|
| Example 10 | Gear-shaped alumina | Pd—La—Ag—Bi | 0.03; palladium chloride | 0.18; silver nitrate | 0.1; lanthanum nitrate | 0.10; bismuth nitrate | 65 | 82 |
| Example 11 | Gear-shaped alumina | Pd—Ce—Ag—Bi | 0.03; palladium chloride | 0.18; silver nitrate | 0.1; cerium nitrate | 0.10; bismuth nitrate | 81 | 77 |
| Example 12 | Gear-shaped alumina | Pd—Nd—Ag—Bi | 0.03 palladium chloride | 0.18; silver nitrate | 0.1; neodymium nitrate | 0.10; bismuth nitrate | 83 | 78 |
| Example 13 | Gear-shaped alumina | Pd—Pr—Ag—Bi | 0.03; palladium chloride | 0.18; silver nitrate | 0.1; praseodymium nitrate | 0.10; bismuth nitrate | 61 | 82 |
| Example 14 | Gear-shaped alumina | Pd—Eu—Ag—Bi | 0.03; palladium chloride | 0.18; silver nitrate | 0.1; europium nitrate | 0.10; bismuth nitrite | 69 | 81 |

TABLE 4-continued

| Example # | Supporter | Catalyst component | Pd (wt. %) | Ag (wt. %) | rare earth metal cocatalyst (wt. %) | Bi (wt. %) | Acetylene conversion(%) | Ethylene selectivity(%) |
|---|---|---|---|---|---|---|---|---|
| Example 15 | Gear-shaped alumina | Pd—Y—Ag—Bi | 0.03; palladium chloride | 0.18; silver nitrate | 0.1; yttrium nitrate | 0.10; bismuth nitrate | 90 | 71 |

Example 16

300 g of gear-shaped alumina supporter was loaded successively with lanthanum nitrate, potassium hydrate, palladium chloride, silver nitrate and bismuth nitrate by impregnating with the corresponding aqueous solution and drying respectively. After calcining, a 0.032 wt. % Pd–0.1 wt. % K–1 wt. % La–0.03 wt. % Ag–0.03 wt. % Bi/alumina catalyst was obtained.

Example 17

300 g of gear-shaped alumina supporter was impregnated with aqueous solutions of potassium carbonate and lanthanum nitrate at the same time, then dried and calcined to obtain a K—La-loaded supporter. The K—La-loaded supporter was loaded simultaneously with palladium nitrate, silver nitrate, bismuth nitrate. After calcining, a 0.032 wt. % Pd–0.1 wt. % K–0.3 wt. % La–0.01 wt. % Ag–0.03 wt. % Bi/alumina catalyst was obtained.

The catalysts of Example 16 and 17 were tested in an industrial sideline unit respectively. 200 ml of the catalyst was packed into a tubular reactor. After displacing the reactor with nitrogen gas, a $C_2$–$C_3$ fraction from the top of pre-de-propanizer of the front end hydrogenation process in ethylene cracking procedure was passed through the reactor in which the fraction contained 0.4–0.7 mol % of acetylene, 0.4–0.6 mol % of MAPD (propyne+propadiene), 500–2000 ppm of carbon monoxide, 8–14 mol % of hydrogen, 25–31 mol % of methane, 4–6 mol % of ethane, 45–50 mol % of ethylene, and a little amount of propane. The above hydrogenation reaction was conducted under the following conditions: inlet temperature of reactor: 70° C., space velocity: 20,000 $hr^{-1}$. The results were shown in table 5.

TABLE 5

| Example # | Supporter | Main catalyst Pd (wt. %) | Rear earth metal Cocatalyst (wt. %) | K (wt. %) | Ag (wt. %) | Bi (wt. %) | outlet acetylene ($10^{-4}$ mol) | Ethylene Selectivity (%) | MAPD Conversion (%) | MAPD selectivity (%) |
|---|---|---|---|---|---|---|---|---|---|---|
| Example 16 | Gear-shaped alumina | 0.032; palladium nitrate | 1; lanthanum nitrate | 0.1; potassium hydrate | 0.03; silver nitrate | 0.03; bismuth nitrate | <1 | >70 | >50 | >70 |
| Example 17 | Gear-shaped alumina | 0.032: palladium nitrate | 0.3; lanthanum nitrate | 0.1; potassium carbonate | 0.01; silver nitrate | 0.03; bismuth nitrate | <1 | >50 | >50 | >70 |

The results shown in table 5 indicate that the catalyst of the present invention could be used not only to remove acetylene from feedstock, but also to remove propyne and propadiene existing in feedstock at the same time.

What is claimed is:

1. A selective hydrogenation catalyst for selectively hydrogenating an unsaturated hydrocarbon, which comprises the following active components loaded on a porous inorganic support based on the total weight of catalyst:

(1) 0.001–1% of at least one element selected from the group consisting of Pt, Pd, Ni, Ru, Co, and Rh;
(2) 0.001–10% of at least one element selected from the group consisting of Ag, Cu, Zn, K, Na, Mg, Ca, Be, Sn, Pb, Sr, Ba, Cd, Ra, Fe, Mn, Zr, Mo, and Ge;
(3) 0.1–1.5% of at least one of a rare earth metal; and
(4) 0.03–5% of Bi; wherein the rare earth metal is selected from the group consisting of Sc, Y, and Lanthanides in Group IIIB of the periodic table of elements.

2. The catalyst according to claim 1, wherein the weight percent of the active component (1) is 0.008–0.3%, based on the total weight of catalyst.

3. The catalyst according to claim 1, wherein the weight percent of the active component (1) is 0.01–0.15%, based on the total weight of catalyst.

4. The catalyst according to claim 1, wherein the weight percent of the active component (2) is 0.01–2%, based on the total weight of catalyst.

5. The catalyst according to claim 1, wherein the weight percent of the active component (4) is 0.03–1%, based on the total weight of catalyst.

6. The catalyst according to claim 1, wherein the active component (1) is Pd.

7. The catalyst according to claim 6, wherein the thickness of Pd layer of the catalyst is 5–30 μm.

8. The catalyst according to claim 1, wherein the active component (2) is Ag.

9. The catalyst according to claim 1, wherein the active component (2) is Ag and K.

10. The catalyst according to claim 1, wherein the active component (2) is Ag and Na.

11. The catalyst according to claim 1, wherein the rare earth metal is selected from the group consisting of La, Ce, Pr, Nd, Pm, Sm, Eu, Gd, Tb, Dy, Ho, Er, Tm, Yb, Lu, and mixtures thereof.

12. The catalyst according to claim 1, wherein the rare earth metal is La and/or Nd.

13. The catalyst according to claim 1, wherein the support is selected from the group consisting of diatomaceous earth, spinel, $SiO_2$, $TiO_2$ $Al_2O_3$, and two or more combinations thereof, and the shape of the support is granular, spherical, gear-shaped, laminar, or strip, and has a specific surface area of 1–200 m²/g.

14. The catalyst according to claim 1; wherein the support is selected from the group consisting of $Al_{2O3}$, $TiO_2$ and $SiO_2$ and the shape of the support is gear-shaped, and has a specific surface area of 2–120 m²/g.

15. The catalyst according to claim 1, wherein the shape of support is gear-shaped, and has a specific surface area of 2–50 m²/g.

16. A process for preparing a catalyst according to claim 1, wherein the rare earth metal component (3) is loaded first onto the support, or the rare earth metal component (3) and the component (2) are loaded concurrently first onto the support, and then other active components are loaded stepwise or concurrently onto the support.

17. A process for selectively hydrogenating alkyne and diolefin having two to four carbon atoms in $C_2$ fraction or $C_3$ fraction from a petroleum hydrocarbon thermal cracking process into olefine, which process comprises passing the alkyne and diolefin having two to four carbon atoms in $C_2$ fraction or $C_3$ fraction and hydrogen gas into a reactor loaded with a catalyst according to claim 1.

18. A process for selectively hydrogenating alkyne and diolefin having two to four carbon atoms in $C_2$ fraction or $C_3$ fraction from a petroleum hydrocarbon thermal cracking process into olefin, which process comprises passing the alkyne and diolefin having two to four carbon atoms in $C_2$ fraction or $C_3$ fraction and hydrogen gas into a reactor loaded with a catalyst according to claim 9.

19. A process for selectively hydrogenating alkyne and diolefin having two to four carbon atoms in $C_2$ fraction or $C_3$ fraction from a petroleum hydrocarbon thermal cracking process into olefin, which process comprises passing the alkyne and diolefin having two to four carbon atoms in $C_2$ fraction or $C_3$ fraction and hydrogen gas into a reactor loaded with a catalyst according to claim 10.

* * * * *

UNITED STATES PATENT AND TRADEMARK OFFICE
CERTIFICATE OF CORRECTION

PATENT NO. : 6,822,127 B2
DATED : November 23, 2004
INVENTOR(S) : Wei Dai et al.

It is certified that error appears in the above-identified patent and that said Letters Patent is hereby corrected as shown below:

Title page,
Item [57] ABSTRACT,
Line 1, "seletive" should read -- selective --.

Column 15,
Line 4, change "$Al_{2O3}$," should read -- $Al_2O_3$, --.

Column 16,
Lines 2 and 9, change "$C_2$fraction" to -- $C_2$ fraction --.

Signed and Sealed this

Fourteenth Day of June, 2005

JON W. DUDAS
*Director of the United States Patent and Trademark Office*